(12) United States Patent
Tallarida et al.

(10) Patent No.: US 12,403,267 B2
(45) Date of Patent: *Sep. 2, 2025

(54) DEVICES AND METHODS FOR INSTALLATION AND REMOVAL OF A NEEDLE TIP OF A NEEDLE

(71) Applicant: VERSAGO VASCULAR ACCESS, INC., West Bridgewater, MA (US)

(72) Inventors: Steven J. Tallarida, Mansfield, MA (US); Richard P. Rodgers, Hudson, MA (US); John M. Butziger, East Greenwich, RI (US)

(73) Assignee: VERSAGO VASCULAR ACCESS, INC., West Bridgewater, MA (US)

( * ) Notice: Subject to any disclaimer, the term of this patent is extended or adjusted under 35 U.S.C. 154(b) by 101 days.

This patent is subject to a terminal disclaimer.

(21) Appl. No.: 18/135,636

(22) Filed: Apr. 17, 2023

(65) Prior Publication Data

US 2024/0082510 A1 Mar. 14, 2024

Related U.S. Application Data

(63) Continuation of application No. 16/724,632, filed on Dec. 23, 2019, now Pat. No. 11,628,261, which is a continuation of application No. 15/301,498, filed as application No. PCT/US2015/024256 on Apr. 3, 2015, now Pat. No. 10,512,734.

(60) Provisional application No. 61/974,807, filed on Apr. 3, 2014.

(51) Int. Cl.
*A61M 5/34* (2006.01)
*A61M 39/02* (2006.01)
*A61M 5/142* (2006.01)

(52) U.S. Cl.
CPC ............ *A61M 5/343* (2013.01); *A61M 5/346* (2013.01); *A61M 39/0208* (2013.01); *A61M 39/0247* (2013.01); *A61M 2005/14284* (2013.01)

(58) Field of Classification Search
CPC .... A61M 2005/14284; A61M 39/0208; A61M 39/0247; A61M 5/343; A61M 5/346
See application file for complete search history.

(56) References Cited

U.S. PATENT DOCUMENTS

| | | | | |
|---|---|---|---|---|
| 4,096,896 A | * | 6/1978 | Engel | B25B 15/00 81/177.85 |
| 5,013,316 A | * | 5/1991 | Goble | A61F 2/0811 606/916 |
| 5,141,520 A | * | 8/1992 | Goble | A61B 17/0401 606/232 |

(Continued)

*Primary Examiner* — Quynh-Nhu H. Vu
(74) *Attorney, Agent, or Firm* — Grossman, Tucker, Perreault & Pfleger, PLLC

(57) ABSTRACT

The present disclosure provides medical devices, particularly medical grade needles with removable tips, as well as methods of needle tip installation and removal, and devices therefor. Needle tip installation and removal devices may include needle tip installation and removal tools and kits, including hand held and manipulated tools that facilitate the installation and removal of needle tips, particularly on vascular access port needles. Such installation and removal devices may provide more expedient hook up of the access port for the therapy. Also, the installation and removal of the needle tips may be conducted in a more sterile manner.

21 Claims, 10 Drawing Sheets

(56) References Cited

U.S. PATENT DOCUMENTS

| | | | | |
|---|---|---|---|---|
| 5,954,723 | A * | 9/1999 | Spetzler | A61B 17/8872 606/309 |
| 5,971,987 | A * | 10/1999 | Huxel | A61L 31/06 606/104 |
| 5,975,815 | A * | 11/1999 | Zierpka | B25B 23/0035 279/22 |
| 6,056,751 | A * | 5/2000 | Fenton, Jr. | A61B 17/0401 606/232 |
| 6,863,072 | B1 * | 3/2005 | Sinnott | A61F 2/0805 128/892 |
| 7,399,299 | B2 * | 7/2008 | Daniel | A61B 18/148 606/41 |
| 7,846,167 | B2 * | 12/2010 | Garcia | A61B 17/8863 606/104 |
| 10,512,734 | B2 * | 12/2019 | Tallarida | A61M 39/0208 |
| 11,628,261 | B2 * | 4/2023 | Tallarida | A61M 39/0247 604/506 |
| 2013/0274814 | A1 * | 10/2013 | Weiner | A61B 17/7291 606/301 |

* cited by examiner

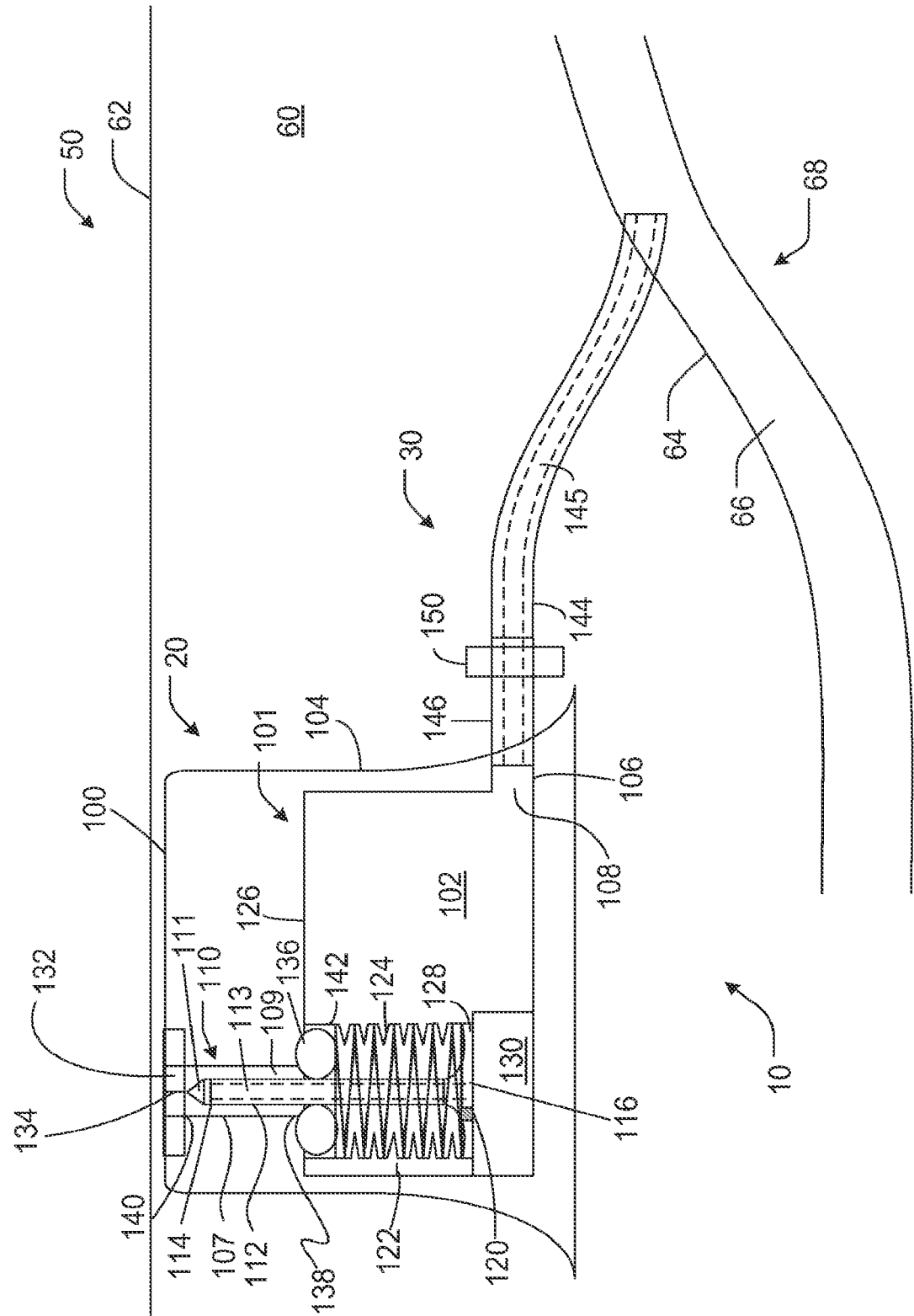

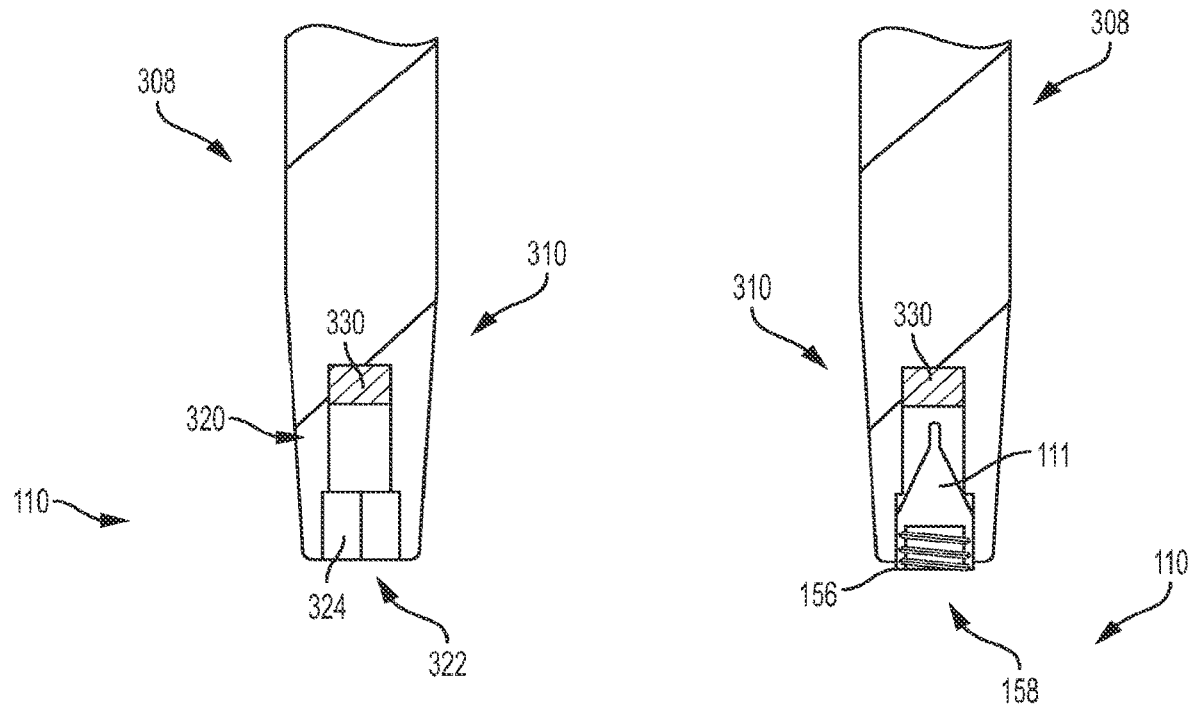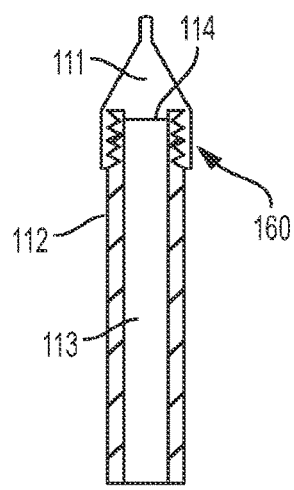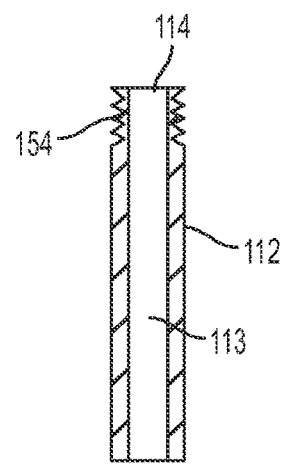
FIG. 5A  FIG. 5B

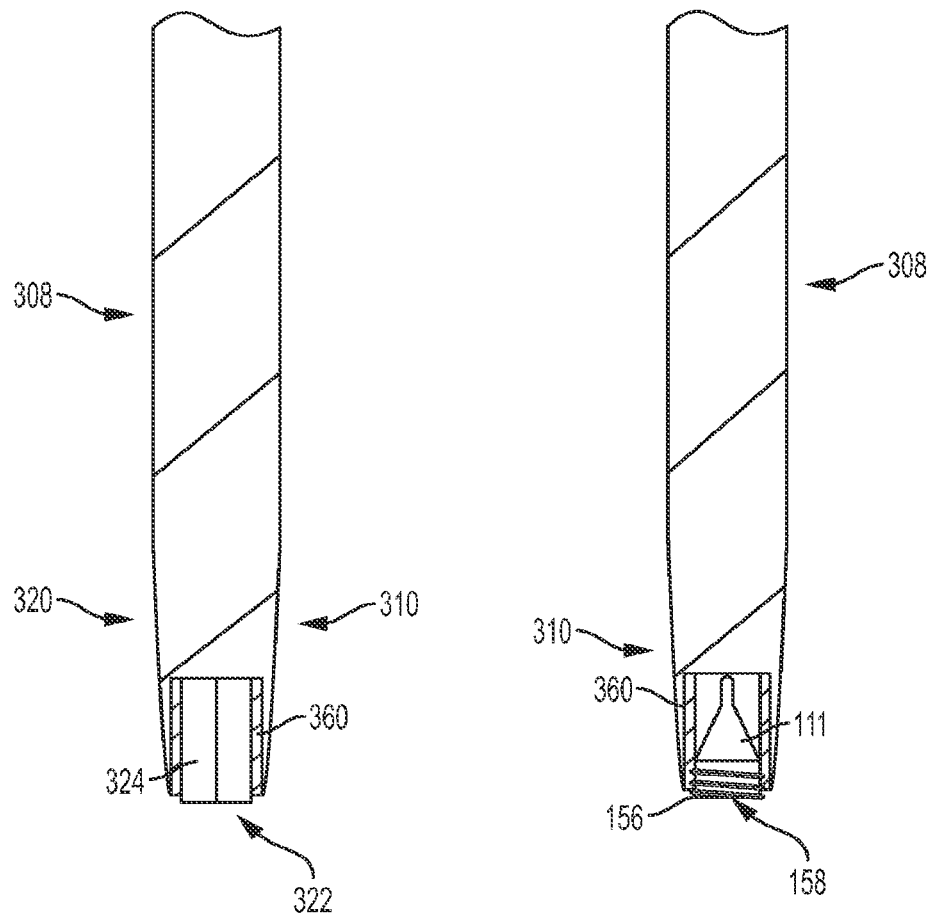
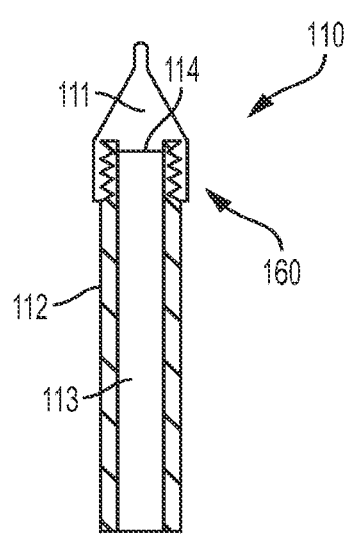
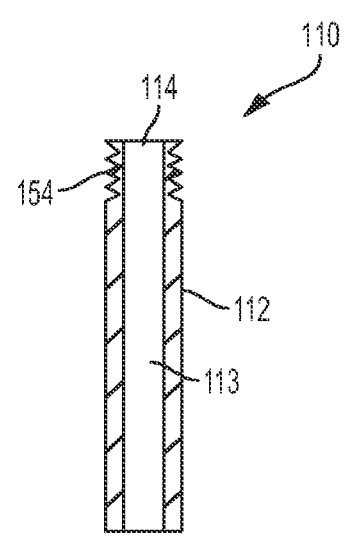
FIG. 7A  FIG. 7B

DEVICES AND METHODS FOR INSTALLATION AND REMOVAL OF A NEEDLE TIP OF A NEEDLE

CROSS REFERENCE TO RELATED APPLICATIONS

This non-provisional patent application is a continuation of U.S. application Ser. No. 16/724,632, filed Dec. 23, 2019, now U.S. Pat. No. 11,628,261, which is a continuation of U.S. application Ser. No. 15/301,498, filed Oct. 3, 2016, now U.S. Pat. No. 10,512,734, which is a national stage (35 U.S.C. 371) application of PCT patent application no. PCT/US2015/024256, filed Apr. 3, 2015, which claims the benefit of U.S. provisional application No. 61/974,807, filed Apr. 3, 2014.

FIELD

The present disclosure relates to medical devices and more particularly to medical grade needles with removable tips, methods of needle tip installation and removal, and devices therefor.

BACKGROUND

Medical patients, such as oncology patients, hemodialysis patients and hematology patients, may be subject to frequent fluid infusion treatments and/or fluid extraction treatments. Fluid infusion treatments may deliver medicaments (e.g. pharmaceutical products; therapeutic drugs), bodily fluid (e.g. blood), nutrients, contrasting agents, dialysis fluid and other liquid compositions to the body, while fluid extraction treatments may remove fluids such as dialysis fluid, bodily fluid (e.g. blood as part of phlebotomy) and other liquid compositions from the body. The fluid infusion treatment and fluid extraction treatment may be part of a fluid exchange treatment, such as dialysis.

Many fluid treatments involve the use of an indwelling catheter with transgresses out of the body. However, where the catheter exits the body, there may be an increased risk of infection. In order to reduce the likelihood of infection, certain medical application may be able to utilize a vascular access port implanted beneath the cutaneous tissue (skin) of the patient/body.

An implanted vascular access port may include an access point, such as a septum. The septum may be formed of a self-healing silicone material. External access to the implanted vascular access port may be accomplished by inserting the needle through the patient's skin and through the septum of the implanted port. However, a clinician needs to properly target the access port and, as a result, multiple needle sticks may be required to properly locate and access the access port, which may add discomfort to the patient. The access port is coupled to an indwelling catheter, which is inserted into a vein, such as a jugular vein, subclavian vein or superior vena cava.

SUMMARY

Access to the implanted vascular access port may be accomplished by extending a hollow needle, particularly with a removable closed tip, from within the access port through the skin. The removable closed tip may keep the needle lumen closed to the ingress of body fluid while the port is not in use. Once the needle has raised (penetrated) through the skin, the removable closed tip may be removed to gain access to the lumen thereof for the infusion of fluids into the patient and/or extraction of fluids from the patient as part of a medical diagnostic and/or therapeutic treatment. Such needle tips may be replaced with a sterile tip to reduce the likelihood of infection to the patient.

The present disclosure provides medical devices, particularly medical grade needles with removable tips, as well as methods of needle tip installation and removal, and devices therefor. Needle tip installation and removal devices may include needle tip installation and removal tools and kits, including hand held and manipulated tools that facilitate the installation and removal of needle tips, particularly on vascular access port needles. Such installation and removal devices may provide more expedient hook up of the access port for therapy. Also, the installation and removal of the needle tips may be conducted in a more sterile manner.

In at least one embodiment, a medical device is provided which comprises at least one needle tip having a pointed closed end; and at least one tool configured to install the at least one needle tip on a needle shaft, the tool comprising a tool body having a proximal end and a distal end, and a needle tip holder located at the distal end of the tool, the needle tip holder configured to hold the needle tip during an installation of the needle tip on the needle shaft. The at least one needle tip and the at least on tool may be components of a sterilized medical device kit.

In at least one embodiment, the at least one need tip may be securable to the needle shaft by a positive mechanical engagement connection, such as provided by a threaded connection. In such instance, the at least one needle tip may comprise a needle shaft receptacle to receive a portion of the needle shaft; the needle shaft receptacle may include needle shaft receptacle threads; the needle shaft may include needle shaft threads; and the at least one needle tip may be securable to the needle shaft by threaded engagement of the needle shaft receptacle threads of the needle tip with the needle shaft threads of the needle shaft.

In at least one embodiment, the needle tip holder may comprise a needle tip receptacle configured to receive the needle tip, and the needle tip receptacle may comprise a mating portion configured to mate with a mating portion of the needle tip.

In at least one embodiment, the mating portion of the needle tip receptacle may be configured to mate with the mating portion of the needle tip such that, when the tool is rotated about a longitudinal axis of rotation, both the needle tip receptacle and the needle tip rotate about the longitudinal axis of rotation.

In at least one embodiment, the mating portion of the needle tip receptacle may have a polygonal shape; and the mating portion of the needle tip may have a polygonal shape which fits inside the polygonal shape of the needle tip receptacle.

In at least one embodiment, the needle tip receptacle of the needle tip holder may be configured to hold the needle tip during the installation of the needle tip on the needle shaft.

In at least one embodiment, the needle tip receptacle may be configured to hold the needle tip during the installation of the needle tip on the needle shaft with a positive mechanical engagement connection formed with the needle tip.

In at least one embodiment, the at least one needle tip may include needle tip threads; the needle tip receptacle may include needle tip receptacle threads; and the positive mechanical engagement may be formed by threaded engagement of the needle tip threads with the needle tip receptacle threads.

In at least one embodiment, the at least one needle tip may include at least one needle tip ridge and/or at least one needle tip groove; In at least one embodiment, the needle tip receptacle includes at least one needle tip receptacle ridge and/or at least one needle tip receptacle groove; and the positive mechanical engagement may be formed by positive mechanical engagement of the at least one needle tip ridge with the at least one needle tip receptacle groove and/or engagement of the at least one needle tip groove with the at least one needle tip receptacle ridge.

In at least one embodiment, the positive mechanical engagement may be formed by a portion of the at least one needle tip which overlaps a portion of the needle tip receptacle in a plane transverse to a longitudinal axis of the tool.

In at least one embodiment, the needle tip receptacle may be configured to hold the needle tip during the installation of the needle tip on the needle shaft with a friction fit connection formed with the needle tip.

In at least one embodiment, the needle tip receptacle may include an elastically deformable member; and the friction fit connection may be formed by elastic deformation of the elastically deformable member when the needle tip is in the needle tip receptacle.

In at least one embodiment, the needle tip receptacle may be configured to hold the needle tip during the installation of the needle tip on the needle shaft with a magnetic force applied to the needle tip.

In at least one embodiment, the needle tip receptacle may include a magnet; and the needle tip may comprise a magnetic material.

In at least one embodiment, the needle tip receptacle may be configured to hold the needle tip during the installation of the needle tip on the needle shaft with a vacuum force applied to the needle tip.

In at least one embodiment, the needle tip receptacle may be in fluid communication with a vacuum passage through which a vacuum is drawn with a vacuum generating device.

In at least one embodiment, a method of medical treatment may be provided, with the method comprising extending a needle located beneath skin of a host such that the needle extends through the skin of the host from beneath the skin of the host, wherein the needle is coupled to an access port implanted beneath the skin of the host and the needle comprises a first removable needle tip secured to a needle shaft; removing the first removable needle tip from the needle shaft with a first needle tip tool to expose a lumen of the needle; administering medical treatment to the host via the lumen of the needle; installing the first removable needle tip or a second removable needle tip on the needle shaft with the first needle tip tool or a second needle tip tool; and retracting the needle beneath the skin of the host.

FIGURES

The above-mentioned and other features of this disclosure, and the manner of attaining them, may become more apparent and better understood by reference to the following detailed description of embodiments described herein taken in conjunction with the accompanying drawings, wherein:

FIG. 1A is a cross-sectional view of a medical device comprising an access port and a catheter; with a needle of the access port including a removable needle tip in a concealed (retracted) position relative to access port body;

FIGS. 5A and 5B are cross sectional side views of one embodiment of a needle tip installation and removal tool, and needle, according to the present disclosure, with the needle tip secured with the needle in FIG. 5A, and the needle tip removed from the needle and held by the tool in FIG. 5B;

FIGS. 7A and 7B are cross sectional side views of another embodiment of a needle tip installation and removal tool, and needle, according to the present disclosure, with the needle tip secured with the needle in FIG. 7A, and the needle tip removed from the needle and held by the tool in FIG. 7B;

DETAILED DESCRIPTION

Figure 1B:
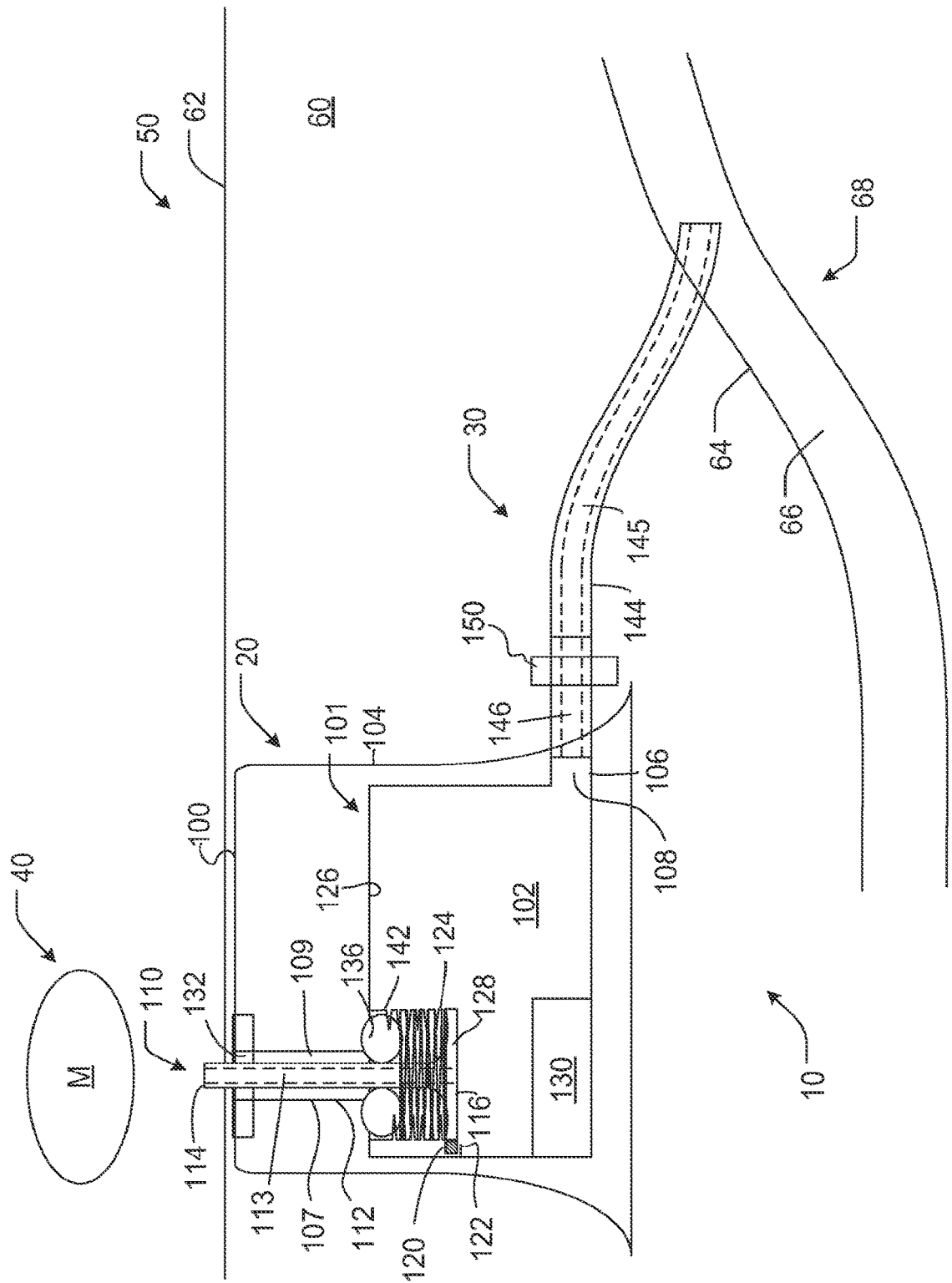
FIG. 1B is a cross-sectional view of the embodiment of the medical device of FIG. IA; with the needle of the access port in an exposed (extended) position relative to access port body and the removable needle tip removed.

It is to be understood that this disclosure is not limited in its application to the details of construction and the arrangement of components set forth in the following description or illustrated in the drawings. The invention(s) herein are capable of other embodiments and of being practiced, or of being carried out, in various ways. Also, it should be understood that the phraseology and terminology used herein is for the purpose of description and should not be regarded as limiting. The use of "including," "comprising." or "having" and variations thereof herein is meant to encompass the items listed thereafter and equivalents thereof as well as additional items. Unless limited otherwise, the terms "connected," "coupled." and "mounted," and variations thereof which may be used herein are used broadly and encompass direct and indirect connections, couplings, and mountings. In addition, the terms "connected" and "coupled" and variations thereof are not restricted to physical or mechanical connections or couplings. Also, spatial references such as "above," "below," "top," "bottom," "horizontal," "vertical," "right," "left," and the like are meant to be understood in relation to the orientation of the device and components thereof as illustrated in the figure being described, and are interchangeable upon spatial reorientation of the device.

By way of general overview, the present disclosure provides medical devices, systems and methods, and more particularly provides indwelling access devices, systems and methods which may comprise an implantable, subcutaneous, indwelling access port, which may be coupled with an implantable, subcutaneous, indwelling catheter within a body, particularly a human body. The access port may include an access port body containing an exposable/concealable internal needle that may extend/retract from the access port body to expose/conceal the internal needle.

The present disclosure also provides medical grade needles with removable tips, as well as methods of needle tip replacement, particularly installation and removal, and devices therefor. Needle tip replacement (installation and removal) devices may include needle tip removal tools and kits, including hand held and manipulated tools that facilitate the installation and removal of needle tips, particularly on access port needles, such as for vascular access ports.

Referring now to the figures, and in particular FIGS. 1A and 1B, there is shown a first embodiment of a medical device 10 according to the present disclosure implanted in a body of a host 50, such as a patient or other subject, who may be undergoing medical treatment or diagnosis. Medical device 10 may comprise an implantable (subcutaneous), indwelling access port 20 and an implantable (subcutaneous), indwelling catheter 30 coupled to the access port 20. As shown, the medical device 10 is implanted beneath the surface 62 of tissue 60, such as cutaneous (skin) tissue, and the indwelling catheter 30 may extend from the access port 20 through the wall 64 and into a lumen 66 of a blood vessel 68 in the tissue 60 of the host 50. In such manner, lumen 145 of catheter body 144 and lumen 66 of blood vessel 68 are in fluid communication. In such application, access port 20 may be understood to comprise a vascular access port.

As shown in FIG. 1A, the access port 20 includes a pointed, closed tip, hollow needle 110 contained and housed within access port body 100. As shown in FIG. 1A, the needle 110 is in a retracted position relative to the access port body 100, and may include a pointed, removable, atraumatic, dialator tip 111 removably coupled to a distal end 114 (relative to the access port 20) of the needle shaft 112, which closes the distal end of shaft lumen 113. As shown in FIG. 1B, needle 110 is in an extended position relative to the access port body 100, and the removable pointed tip 111 has been removed to expose and provide access to lumen 113.

The needles 110 contemplated herein may particularly have gauge sizes in a range of 12 gauge to 22 gauge (e.g. 12, 13 14, 15, 16, 17, 18, 19, 20, 21 or 22 gauge). However the needles may also have other sizes, small or larger. The needles 110 may exhibit an outer diameter in the range of 0.1 mm to 4.6 mm, including all values and increments therein. In addition, the needles 110 may exhibit an inner diameter in the range of 0.08 mm to 4.0 mm, including all values and increments therein. Furthermore, the needles 110 may exhibit a nominal wall thickness in the range of 0.002 mm to 0.4 mm, including all values and increments therein. The needles 110 may be formed of stainless steel or other materials.

As explained in greater detail herein, the removable tip 111 may be removably secured to the needle shaft 112, such as by threaded engagement of opposing complementary threads on each component. For example, referring briefly to FIG. 5B, the distal end portion of the needle shaft 112 may include external threads 154 which mate and engage within internal threads 156 of needle shaft receptacle 158 of needle tip 111. As such, when needle tip 111 is rotated in a first direction (e.g. clockwise or counter-clockwise) relative to the needle shaft 112, the needle tip 111 may be installed (mechanically engage) on needle shaft 112. Conversely, when needle tip 111 is rotated in a second direction opposite the first direction (e.g. counter-clockwise if the first direction is clockwise and clockwise if the first direction is counter-clockwise), the needle tip 111 may be removed (mechanically disengage) from needle shaft 112. Stated another way, the complementary threads 154, 156 may be either right-hand threads or left-hand-threads.

Referring back to FIGS. 1A and 1B, a proximal end 116 of the needle shaft 112 may be secured within the access port body 100 against inadvertent removal from the access port 20. The needle 110, including either needle tip 1111 and/or needle shaft 112, may be made of a magnetic (ferromagnetic) material, or may include a ferromagnetic material at the distal end 114. Examples of ferromagnetic material include iron, nickel and/or cobalt.

The access port body 100 may include an external surface 104 and an internal fluid flow passage 101 which may allow fluid to flow through the access port 20 in either direction as described herein. Access port body 100 may include a fluid containment chamber 102, which may optionally provide a reservoir for fluid to be stored within the access port 20. The access port 20 may also include first and second bores 106, 107 on different sides of the chamber 102 which provide tubular passages 108, 109, respectively, connecting or providing fluid communication between the chamber 102 and the external surface 104 of the access port 20. Needle 110 may be positioned within bore 107/passage 109 and may extend from and/or retract into the access port body 100 relative to a outer self-closing seal 132, such as a "self healing" silicone septum described below. Thus, within access port body 100, the internal fluid flow passage 101 which allows fluid to pass through access port 30 may be formed by chamber 102, tubular passage 108 and lumen 113 of needle 110.

To extend the needle 110 as shown in FIG. 1B, an actuator 40 comprising a magnet M, such as an electro-magnet, may be positioned closely over (adjacent within about 10 mm, and more particularly within about 5 mm) or on the needle 110, or it may be positioned closely over or on a device to which the needle 110 may attach. When an electric current of a first polarity is provided to magnet M, magnet M may emit an electro-magnetic field arranged with a first polarity which attracts needle 110. The needle 110, being attracted (pulled) towards the magnet M by the electro-magnetic force of the electro-magnetic field, may be exposed by extending outwards from the access port body 100 of the access port 20 towards the magnet M and out of the host 50 by piercing through the skin surface 62 from within tissue 60.

The needle tip 111 of the needle 110 is designed to operate as a dilator during and after the distal (terminal) pointed end of the needle tip 111 (which may be referred to as a pencil tip) has penetrated through tissue 60. With the configuration as shown, the needle tip 111 of the needle dilates the tissue 60 rather than cutting through the tissue 60 to minimize injury.

Alternatively, when it becomes desirable to retract the needle 110 back into the access port body 100 of the access port 20, after the needle tip 111 has been placed on needle shaft 112, an electric current of a second polarity opposite the first polarity (i.e. reverse polarity) is provided to magnet M. Magnet M may then emit an electro-magnetic field arranged with a second polarity which repels the needle 110 from the magnet M, in which case the needle 110 will be pushed away from the magnet M by the force of the electromagnetic field and retract inwards relative to access port body 100 and the host 50 to be concealed. As the needle 110 travels inwards in access port body 100, needle 110 correspondingly retracts and withdraws into cutaneous (skin) tissue 20.

In certain embodiments, after the needle 110 is extended, rotation of the needle 110 may lock the needle 110 in place against retraction. For example, the proximal end 116 of the needle 110 may include a projection 120 that may engage or otherwise cooperate with a needle lock mechanism 122, such as by rotating onto a catch or into a channel, provided in the chamber 102 at a predetermined location.

In addition, in certain embodiments the magnet M may be positioned on or within the device to which the needle 110 may be affixed to administer a given fluid (liquid) composition. For example, the magnet M may be positioned proximal to the lip of a vial, near the vial stopper, or in the tip of a catheter into which distal end 114 of the needle 110 may be asserted.

In certain embodiments, a needle extension biasing mechanism 124, such as a spring, may be positioned between the proximal end 116 of the needle 110 and a chamber wall 126 to retain the needle 110 in the retracted position. As may be appreciated, the force F(s) exerted by the spring 124 on the needle 110 towards the retracted position may be less than the force F(m) exerted by the magnet M, or stated another way, the force F(m) is greater than the force F(s).

In certain embodiments, the needle 110 may include a flare 128 at the proximal end 116 which the spring 124 biases against when compressed and needle 110 is in the extended position. In addition, in certain embodiments, a bumper seal 130 may be provided to receive the proximal end 116 of the needle 110 in the retracted position to cushion retraction of the needle 110. The bumper seal 130 may also function to close the proximal end 116 of the needle lumen 113 to prevent back flow of fluid through the needle 110 when the needle 110 is retracted, particularly in the event the needle 110 does not include pointed tip 111. The bumper seal 130 may be formed into the chamber 126 or may be adhered onto the chamber walls.

In certain embodiments, a self-closing seal 132, such as a "self-healing" silicone septum, may be provided at the outer end 140 of tubular passage 109. This seal 132 may be provided alone, or in addition to the bumper seal 130, provided in the chamber 102. The seal 132 may include a perforation 134 to allow the needle 110 to more easily pass through upon application of the magnetic force by the magnet M of the actuator 40.

In addition, in certain embodiments, an additional seal 136 may be provided at the inner end 138 of tubular passage 109 to prevent backflow of the fluid in the chamber 102 into the tubular passage 109. It may be appreciated that further seals may be provided between the inner end 138 of the tubular passage 109 and the outer end 140 of the tubular passage 109. In other embodiments, an expandable and/or collapsible sleeve 142 may be provided over the spring 124 and/or needle 110 preventing mingling of the fluids in the port with the spring surfaces or the exterior surfaces of the needle 110. The sleeve 142 may be accordion like or in the shape of a bellows.

Indwelling catheter 30, and more particularly catheter body 144 may be removably attached to the access port 20 by a connector 146, or permanently attached to the access port 20 through chemical or mechanical means, including an adhesive, ultrasonic welding, press-fits, etc. The catheter body 144 may be relatively flexible and formed of a composition such as silicone, polyurethane, or other thermoplastic elastomers. In addition, in some embodiments, a metering device 150 may be provided between chamber 102 of the access port 20 and the catheter 30. The metering device 150 may include a valve and allow for control of the flow rate of fluid through the access port 20.

Figure 2:
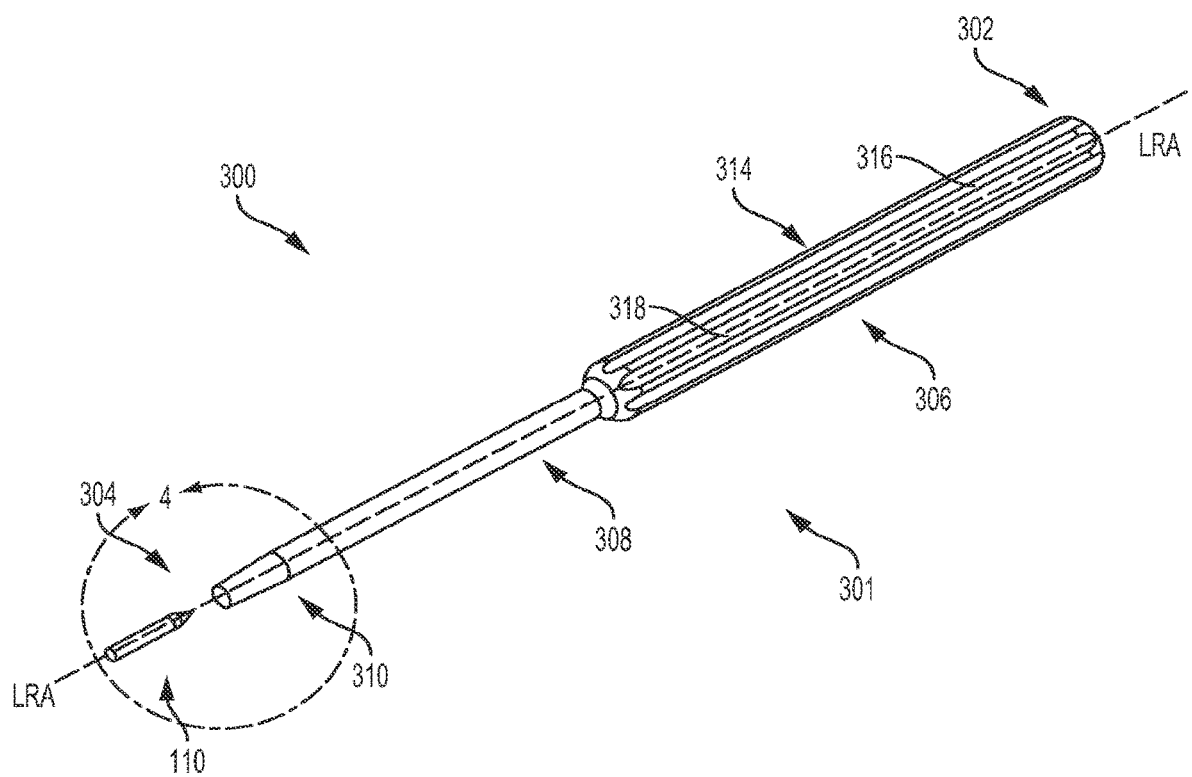
FIG. 2 is a perspective view of an embodiment of a needle tip installation and removal tool according to the present disclosure, with the needle of the access port in alignment therewith.
Figure 3:
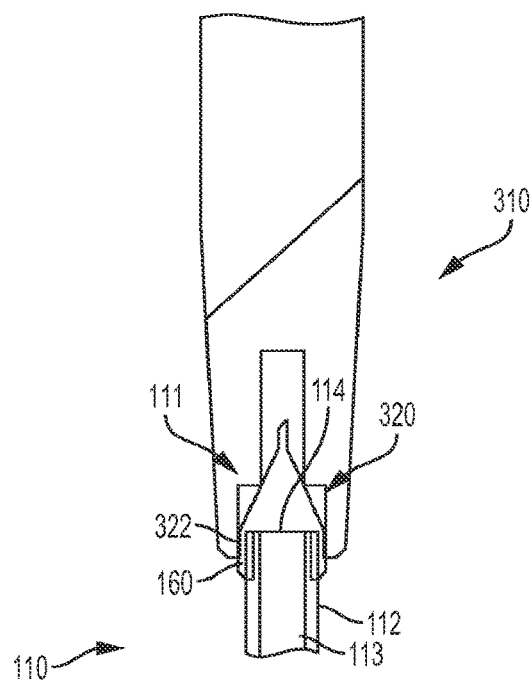
FIG. 3 is a close-up cross-sectional side view of a distal end portion of the needle tip installation and removal tool of FIG. 2 joined with the needle of FIG. 2.
Figure 4:
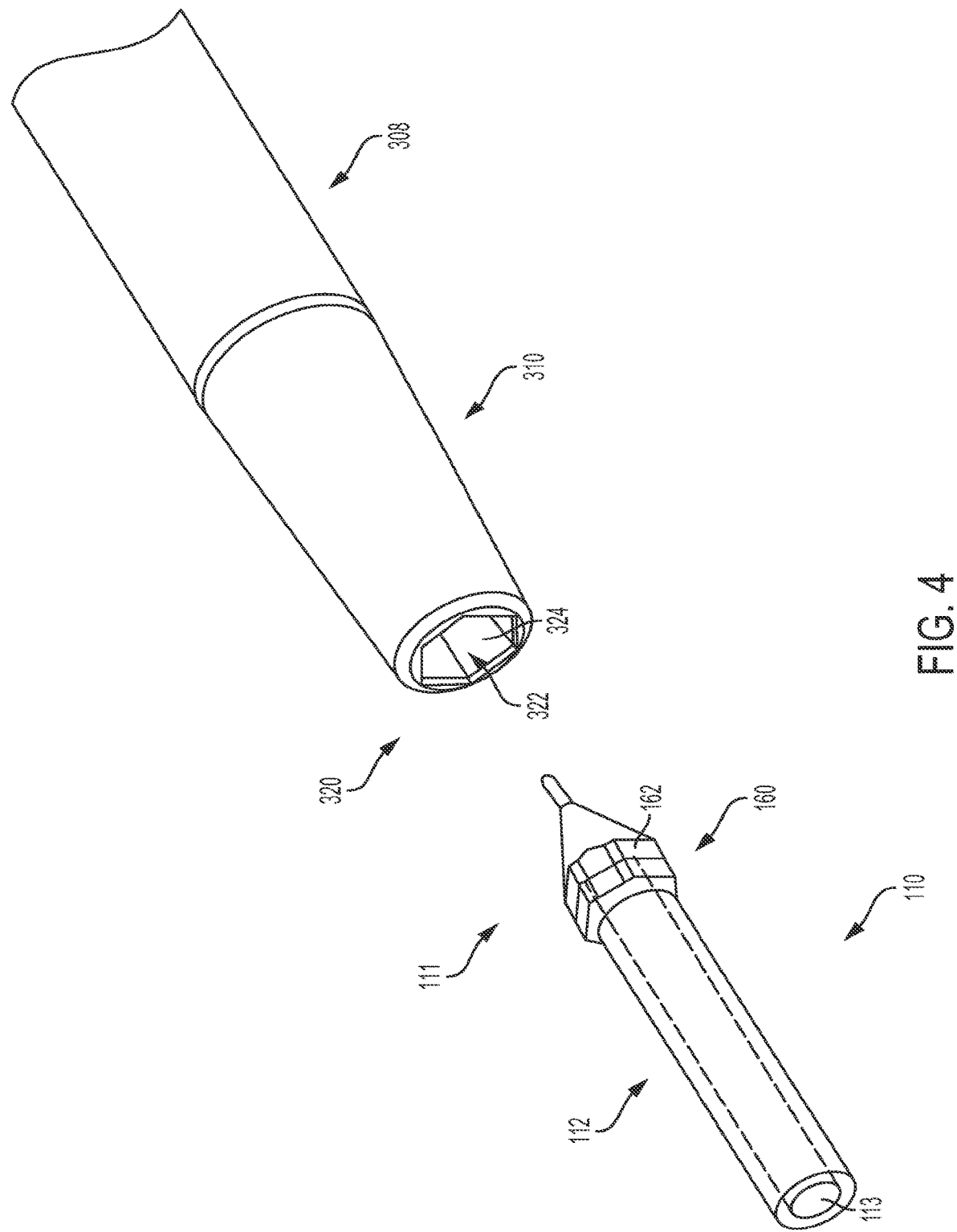
FIG. 4 is a close-up perspective view of a distal end portion of the needle tip installation and removal tool of FIG. 2 and the needle of FIG. 2.

Referring now to FIGS. 2-4, there is shown needle 110 with removable needle tip 111 secured to the needle shaft 112. A hand-held, hand-manipulated, needle tip installation and removal tool 300 for manipulating needle tip 111, particularly installing and removing a needle tip 111 on needle shaft 112 is shown in FIG. 2. Tool 300 comprises an elongated tool body 301 having a proximal end 302 and a distal end 304 (relative to the user of tool 300). Tool body 301 may include an elongated handle 306, a shaft 308 extending from the handle 306, and a needle tip holder 310 located at a distal end of the shaft 308.

The handle 306 may have an ergonomically designed shape which may include gripping features 314 that facilitate the gripping and manipulation of the tool 300 by hand, particularly by the palm and fingers. For example, the handle 306 may include a plurality of equally spaced, elongated, alternating ridges 316 and grooves 318 that may extend along a portion of the length of the handle 306 or substantially the whole length of the handle 306. The handle 306 may generally have a length in a range of 3 to 7 inches, and be the same diameter as the shaft 308 or larger. The shaft 308 may be cylindrical and also have a length of 3 to 7 inches.

The needle tip holder 310 may comprise a tubular (e.g. polygonal, circular) needle tip receptacle 320, located at distal end 304 of the needle tip installation and removal tool 300, configured to receive and accommodate the needle tip 111 which resides at the distal end 114 of a needle shaft 130. The needle tip 111 may have a mating portion 160 configured to mate and interact with a mating portion 322 of the needle tip receptacle 320 of the tool 300 for easy installation onto or removal from the needle shaft 112 (which may also be referred to as a cannula) of the access port 20.

More particularly, the needle tip receptacle 320, particularly the internal sidewall of the mating portion 322, may have a peripheral shape configured to mate and interact with the peripheral shape of the external sidewall of mating portion 160 of the needle tip ill.

Even more particularly, the internal sidewall of the mating portion 322 of the needle tip receptacle 320 and the external sidewall of mating portion 160 of the needle tip 111 may mate and interact such that, when tool 300 is rotated about its longitudinal rotational axis LRA in a first direction (e.g. clockwise) the needle tip 111 may be installed on needle shaft 112, particularly by the internal threads 156 of the needle tip 111 engaging with the external threads 154 of the needle shaft 112. Conversely, when tool 300 is rotated about its longitudinal rotational axis LRA in a second direction opposite the first direction (e.g. counter-clockwise) the needle tip 111 may be removed from needle shaft 112, particularly by the internal threads 156 of the needle tip 111 disengaging from the external threads 154 of the needle shaft 112.

As shown in FIGS. 4, 5A and 5B, the internal sidewall of the mating portion 322 of the needle tip receptacle 320 and the external sidewall of mating portion 160 of the needle tip 111 may each comprise a plurality of planar sections 324 and 162, respectively. The plurality of the planar sections 162 of the mating portion 160 of the needle tip 111 may be arranged around a periphery of mating portion 160 to form a polygonal shape. A shown, the plurality of the planar sections 162 of the mating portion 160 of the needle tip 111 may more particularly form a six-sided (male) polygon, i.e. a hexagon. Similarly, the plurality of the planar sections 324 of the mating portion 322 of the needle tip receptacle 320 may more particularly form a six-sided (female) polygon, i.e. hexagon.

In order to hold needle tip 111 in needle tip holder 310, particularly when the threads 154 of the needle shaft 112 and threads 156 of needle shaft receptacle 158 of needle tip 111 are disengaged during installation or removal of needle tip 111, at least a portion of the needle tip holder 310, and more particularly the needle tip receptacle 320, may be formed by magnet 330, such as an electro-magnet or permanent magnet.

In the foregoing manner, when the needle tip 111 is in needle tip holder 310, the needle tip 111 may be held in the needle tip holder 310, and more particularly the needle tip receptacle 320, by the magnetic force of the magnet 330. In the case of an electro-magnet, the needle tip 111 may be removed from the needle tip receptacle 320 by shutting off the electromagnet or, in the case of a permanent magnet, by exposing the needle tip 111 to an opposite stronger magnetic force. Alternatively, the needle tip 111 may be removed from the needle tip receptacle 320 simply by pulling the needle tip 111 out of needle tip receptacle 320 by hand, against the bias force of the permanent magnet 330.

Figures 6A, 6B:
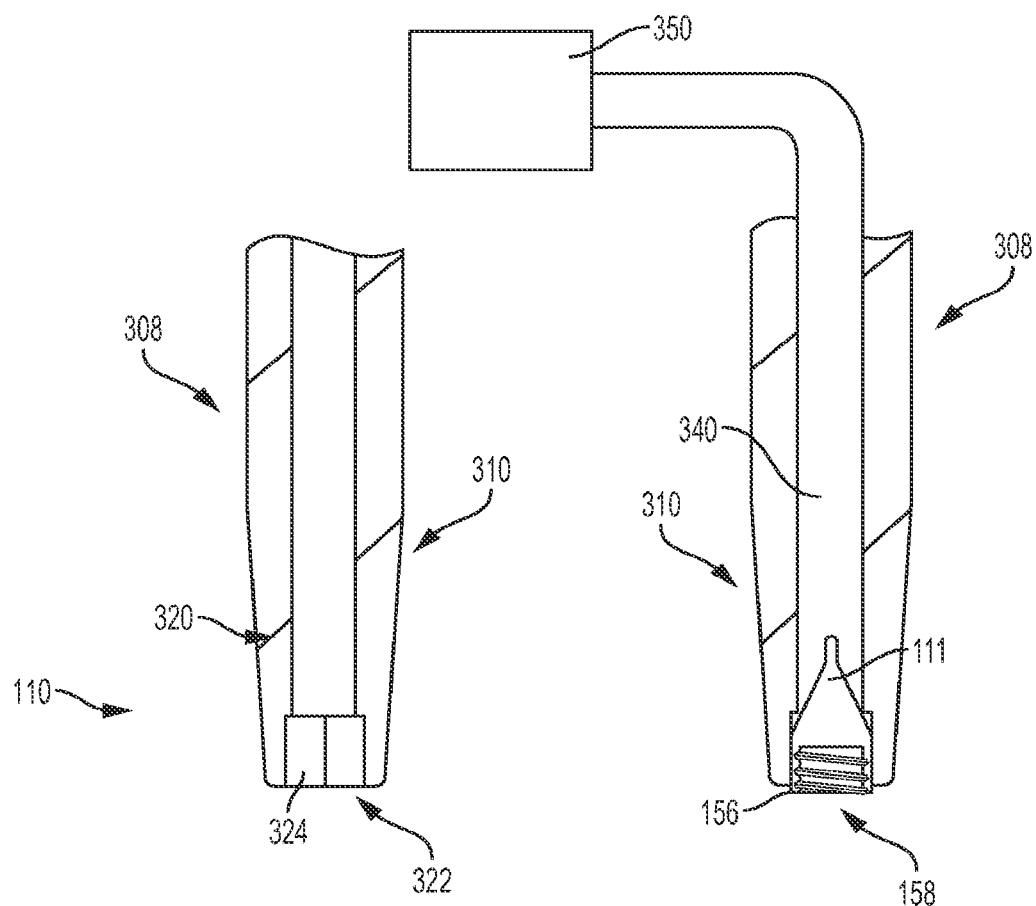
FIGS. 6A and 6B are cross sectional side views of another embodiment of a needle tip installation and removal tool, and needle, according to the present disclosure, with the needle tip secured with the needle in FIG. 6A, and the needle tip removed from the needle and held by the tool in FIG. 6B.

Referring now to FIGS. 6A and 6B, in another embodiment of the present disclosure, in order to hold needle tip 111 in needle tip holder 310, particularly when the threads 154 of the needle shaft 112 and threads 156 of needle shaft receptacle 158 of needle tip 111 are disengaged during installation or removal of needle tip 111, the tool 300 may include a vacuum (pressure below atmospheric pressure) passage 340 which may extend through handle 306, through shaft 308 and to needle holder 310, particularly to needle tip receptacle 320. To provide vacuum to needle holder 310, and more particularly the needle tip receptacle 320, vacuum passage 340 may be in fluid communication with a vacuum device 350, such as a vacuum generating device or vacuum source device, which may be part of tool 300, such as located in handle 306. The needle tip 111 may then be removed from the needle tip receptacle 320 by turning off or reducing the vacuum. Alternatively, the needle tip 111 may be removed from the needle tip receptacle 320 simply by pulling the needle tip 111 out of needle tip receptacle 320 by hand, against the bias force of the vacuum.

Referring now to FIGS. 7A and 7B, in another embodiment of the present disclosure, in order to removably hold needle tip 111 in needle tip holder 310, particularly when the threads 154 of the needle shaft 112 and threads 156 of needle shaft receptacle 158 of needle tip 111 are disengaged during installation or removal of needle tip 111, at least a portion of the needle tip holder 310, and more particularly the mating portion 322 of the needle tip receptacle 320, may form a friction fit (which also may be known as an interference fit or pressure grip fit) connection with the needle tip 111. A friction fit connection may be understood herein as a connection formed between two components which solely relies upon friction to inhibit separation of the components, for example by one of the components being pressed into the other component such that at least one of the components is compressed (deformed) against one another.

In order to provide a friction fit connection, a portion of the needle tip receptacle 320, and more particularly the mating portion 322, may be formed with a smaller dimension than the mating portion 160 of the needle tip 111 to form the friction fit connection. As shown, at least a portion of the mating portion 322 of needle tip receptacle 320 may be formed by an elastically deformable member 360, such as rubber, which may deform (as to enlarge) when the needle tip 111 is located therein to hold the needle tip 111.

Figure 8A:
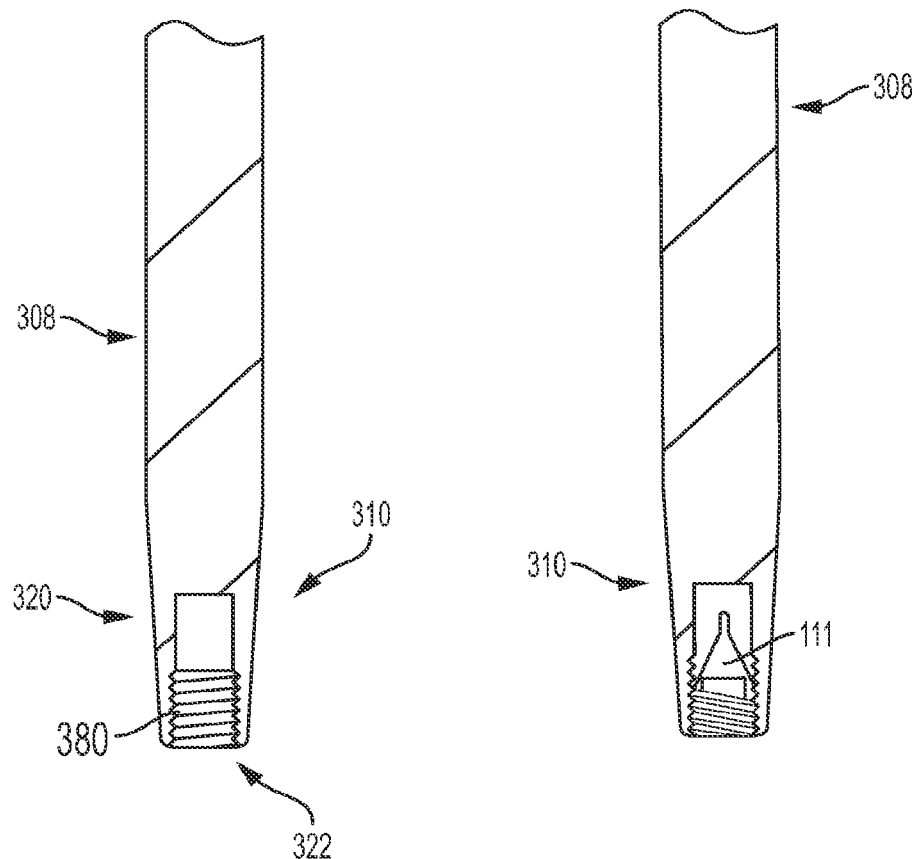
FIGS. 8A and 8B are cross sectional side views of another embodiment of a needle tip installation and removal tool, and needle, according to the present disclosure, with the needle tip secured with the needle in FIG. 8A, and the needle tip removed from the needle and held by the tool in FIG. 8B.
Figure 8B:
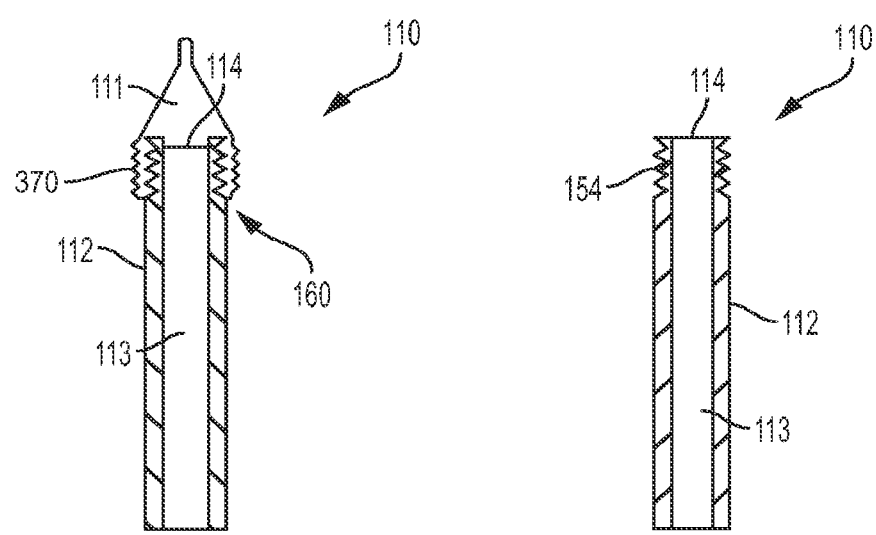

Referring now to FIGS. 8A and 8B, in another embodiment of the present disclosure, in order to hold needle tip 111 in needle tip holder 310, particularly when the threads 154 of the needle shaft 112 and threads 156 of needle shaft receptacle 158 of needle tip 111 are disengaged during installation or removal of needle tip 111, at least a portion of the needle tip receptacle 310, and more particularly the mating portion 322 of the needle tip receptacle 320, may form a positive mechanical connection with the needle tip 111. A positive mechanical engagement connection may be understood herein as a connection formed between the components which does not rely solely on friction to inhibit separation of the components and which includes a mechanical interlock to inhibit separation of the components (e.g. overlapping surfaces).

In order to provide a positive mechanical engagement connection, the mating portion 160 of the needle tip 111 may include external threads 370 which mate and engage within internal threads 380 of the mating portion 322 of the needle tip receptacle 320 of the needle tip holder 310. As such, when tool 300 and the needle tip receptacle 320 are rotated in a first direction (e.g. clockwise or counter-clockwise) relative to the needle tip 111, the needle tip receptacle 320 may mechanically engage with the needle tip 111. Conversely, when tool 300 and the needle tip receptacle 320 are rotated in a second direction opposite the first direction (e.g. counter-clockwise if the first direction is clockwise and clockwise if the first direction is counter-clockwise), the needle tip receptacle 320 may mechanically disengage from the needle tip 111. Stated another way, the threads 370, 380 may be either right-hand threads or left-hand-threads.

If, in the event, the removable tip 111 is positively mechanically engageable to the needle shaft 112 by threaded engagement of threads 156 and threads 154, respectively, and the needle tip receptacle 320 is positively mechanically engageable to the needle tip 111 by threaded engagement of threads 380 and threads 370, respectively, the pairs of threads 156, 154 and 380, 370 should have opposite drive hands. Thus, if threads 156, 154 are right-hand threads, then threads 380, 370 should be left-hand threads, and vice-versa.

In another embodiment, similar to the embodiment of FIGS. 7A and 7B, at least a portion of the needle tip receptacle 320 of the embodiment of FIGS. 8A and 8B may be formed of an elastically deformable material, such as rubber, which may deform (as to enlarge) when the needle tip 111 is located therein to hold the needle tip 111. In such instance, the alternating circumferential ridges and grooves provided by the threads 380 may provide positive mechanical engagement by ratchet or snap fit connection, which may be in addition to or as an alternative to the positively mechanical engagement being provided by threads 380 which are rotationally engageable and disengageable. In such an instance, the ridges and grooves provided by the threads 380 of the needle tip receptacle 320 and threads 370 of the needle tip 111 may now operate linearly as rows of engageable/disengageable teeth for a linear sliding ratchet. More particularly, as the needle tip 111 is pushed into the needle tip receptacle 320, the elastic threads 380 of the of the mating portion 322 of the needle tip receptacle 320 may deform as deformable teeth, such as with a sliding snap fit, allowing the threads 370 of the needle tip 111 to enter the needle tip receptacle 320 past the threads 380 of the needle tip receptacle 320 without requiring rotational action. In such instance, it may be understood that the positive mechanical engagement is formed by a portion of the needle tip 111 which overlaps a portion of the needle tip receptacle 320 in a plane transverse to a longitudinal axis of the tool 300.

For the foregoing positive mechanical engagement embodiment, as well as the friction fit connection, tool 300 may include a passage similar to passage 340 which extends through handle 302, through shaft 308 and to needle holder 310. A push rod may then be inserted into the passage to apply pressure to the needle tip 111 to push the needle tip 111 from the needle tip receptacle 320 and dislodge the tip from the tool 300. Alternatively, a button may be disposed at the proximal end of the handle 306 which, when depressed, may activate a member extending through the passage to dislodge the needle tip 111 from the tool 300.

It should be understood that any of the foregoing structures and methods of retaining needle tip 111 in needle tip holder 310, particularly when the threads 154 of the needle shaft 112 and threads 156 of needle shaft receptacle 158 of needle tip 111 are disengaged during installation or removal of needle tip 111, may be combined into a single tool 300 as suitable. For example, the mating portion 160 of the needle tip 111 and the mating portion 322 of the needle tip receptacle 320 of the needle tip holder 310 may be temporarily retained to one another by releasable positive mechanical engagement/connection or friction fit engagement/connection. Such may be supplemented with magnetic and/or vacuum assist.

It should also be understood that the mating portion 160 of the needle tip 111 and the mating portion 322 of the needle tip receptacle 320 of the needle tip holder 310 may be circular, particularly threaded, as shown in FIGS. 8A and 8B, or non-circular, as shown in FIGS. 2 to 7B, in which case the mating portions may have a polygonal shape (e.g. triangular, quadrilateral (e.g. square), pentagonal hexagonal, heptagonal, octagonal, etc.)

It should also be understood that the mating portion 160 of the needle tip 111 and the mating portion 322 of the needle tip receptacle 320 of the needle tip holder 310 may have one or more circumferential ridges and grooves, particularly provided by threads, as shown in FIGS. 8A and 8B, or have planar sections, as shown in FIGS. 2 to 7B, in which case the mating portions may have a polygonal shape.

Figure 9:
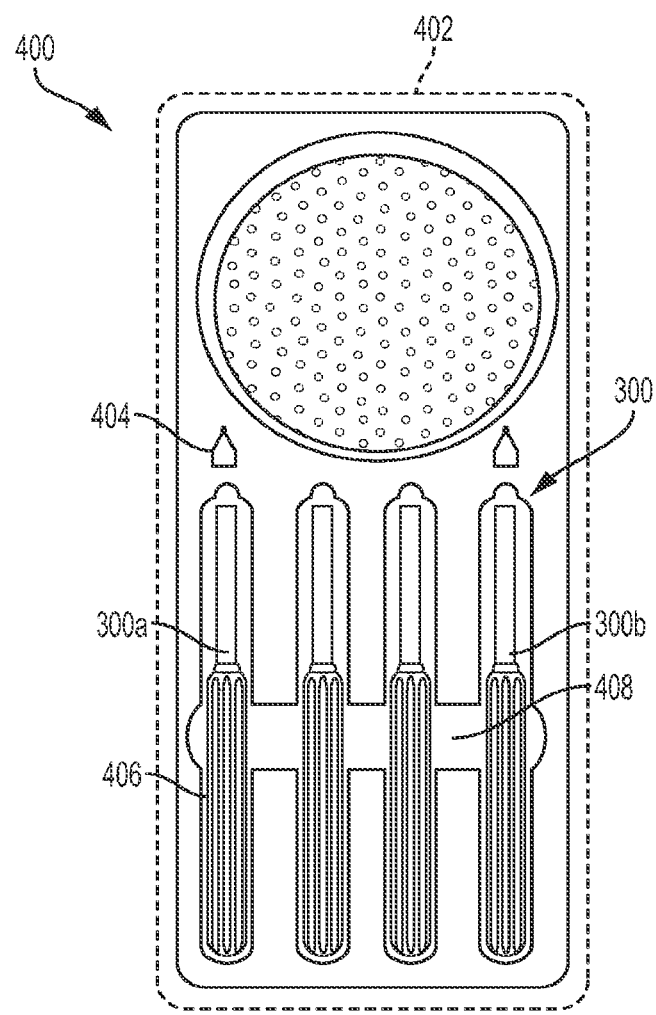
FIG. 9 is a front view of a needle tip installation and removal tool kit according to the present disclosure.
Figure 10:
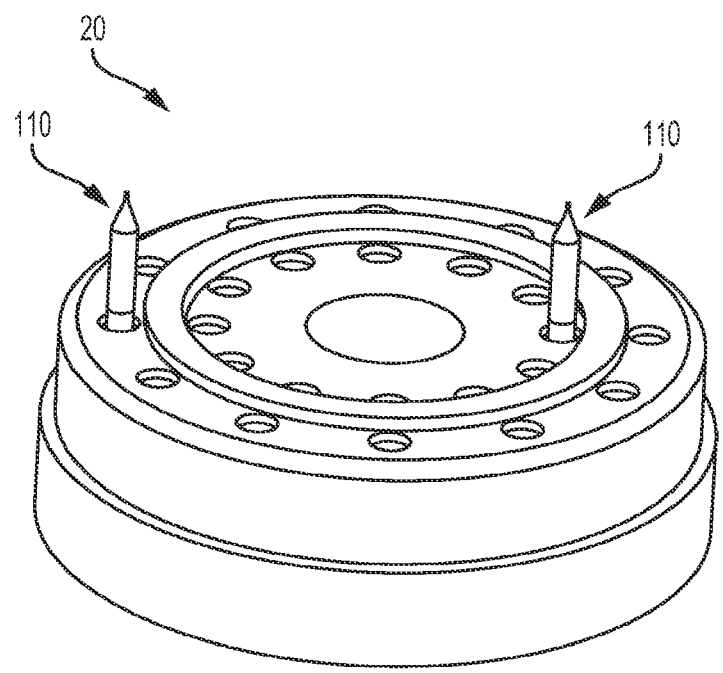
FIG. 10 is a perspective view of a medical device comprising an access port with two needles, with each needle having a removable tip.

Referring to FIG. 9, disposable or reusable kits 400 may be provided specifically configured for single use per operation of the access port 20, particularly with sterile tools 300 and sterile tips 111 residing on a sterile tray 404 sealed with heat sealed sterile packaging 402. Generally, kit 400 may have two or four sterile tools 300. For an access port 20 with only one needle 110, the kit 400 may include a tray 404 including two sterile tools 300 and optionally one sterile tip 111 (one tool 300a to remove the tip 111 and the other tool 300b to install a new tip 111). For an access port 20 with two needles 110, such as an access port 20 for hemodialysis (see FIG. 10), the kit 400 may include a tray 400 including four sterile tools 300 and optionally two sterile tips 111 (two tools 300a to remove the tips 111 and the two tools 300b to install a new tips 111).

The kit 400 may also contain the replaceable sterile tips 111, or these could be provided in their own separate packaging. The tools 300a for removing the tips 111 may be the same or different from the tools 300b for applying the new tips 111. In some embodiments, the tools may be color coded. The tray 404 may contain molded recesses 406 having a shape which contains the tools 300, and a further recess 408 to facilitate the grasping of the tools 300 out of the tray 404. In some embodiments, the needle tips 111 may be preloaded onto the tools 300 so as to be ready to use.

The kits 400 need not contain the tools 300a for the removal of the needle tips 111 as sterility is not essential at that stage of the procedure. Hence, the sterile kit 400 may include at least one tool 300 with the needle tip 100 pre-fitted in the needle tip receptacle 320 of the tool 300b to be applied to the needle shaft 112 of the access port 20 without further manipulation than opening a kit packaging, grasping the tool 300b and applying the tip 111 onto the needle shaft 112. In certain embodiments, the sterile kit 400 includes two tools 300b with each tool 300b having fitted thereon a needle tip 111. In certain embodiments, the sterile kit 400 includes the access port 20.

The tools 300 may be made of material for single use or capable of withstanding autoclaving for further use. The tools 300 may be made of moldable polymer, such as polycarbonate or polypheyleneoxide, or an appropriate metal, such as stainless steel and/or titanium, or other materials depending on the sterilization requirements.

In certain embodiments, the tool 300 may be configured to incorporate the functions of both removal of a needle tip 111 and installation of a new tip 111. Such design may include, for example, a tool 300 that has two needle tip receptacles 320, one on each opposite end, one for removal of needle tips 111 and the other for installation of new tips 111.

In operation, once the access port 20 is in the configuration with the needle 110 protruding from the port 20 and through the skin, a packaging seal of the kit 400 is broken and a first tool 300 is used to remove the first needle tip 111. In the case of an access port with two needles 110, then a second tool 300, or the same tool 300, is used to remove the second needle tip 111.

The exposed needle shaft(s) 112 is/are then connected to the treatment (therapy or diagnostic) device. Once the treatment is completed, a third tool 300, or the same tool 300, is used to install a new sterile tip 111 onto the first needle shaft 112, and, in the case of an access port 20 with two needles 110, then a fourth tool 300, or the same tool 300, is used to install a new sterile tip 111 onto the second needle shaft 112. Hence, to guarantee the best sterile environment during these procedures of accessing the access port 20, it is preferable to use a separate tool 300 for each needle 110 and each operation.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

What is claimed is:

1. A medical device comprising: at least one needle tip having a pointed closed end configured to penetrate tissue, the needle tip configured to be installed on a hollow needle shaft having a fluid flow passage within the needle shaft, and the needle tip configured to be removed from the needle shaft; the needle tip configured to close the fluid flow passage within the needle shaft when the needle tip is installed on the needle shaft, the at least one need tip is securable to the needle shaft by a positive mechanical engagement connection; and at least one tool configured to install the at least one needle tip on the needle shaft, the tool comprising a needle tip holder, the needle tip holder comprising a needle tip receptacle configured to receive the needle tip, including the pointed closed end, therein, and configured to hold the needle tip during an installation of the needle tip on the needle shaft.

2. The medical device of claim 1 wherein: the at least one needle tip and the at least on tool are components of a sterilized medical device kit.

3. The medical device of claim 1 wherein: the positive mechanical engagement connection comprises a threaded connection.

4. The medical device of claim 3 wherein:
the at least one needle tip comprises a needle shaft receptacle to receive a portion of the needle shaft; the needle shaft receptacle includes needle shaft receptacle threads; the needle shaft includes needle shaft threads; and the at least one needle tip is securable to the needle shaft by threaded engagement of the needle shaft receptacle threads of the needle tip with the needle shaft threads of the needle shaft.

5. The medical device of claim 1 wherein: the needle tip receptacle of the needle tip holder comprises a mating portion configured to mate with a mating portion of the needle tip.

6. The medical device of claim 5 wherein: the mating portion of the needle tip receptacle is configured to mate with the mating portion of the needle tip such that, when the tool is rotated about a longitudinal axis of rotation, both the needle tip receptacle and the needle tip rotate about the longitudinal axis of rotation.

7. The medical device of claim 5 wherein: the mating portion of the needle tip receptacle has a polygonal shape; and the mating portion of the needle tip has a polygonal shape which fits inside the polygonal shape of the needle tip receptacle.

8. The medical device of claim 1 wherein: the needle tip receptacle of the needle tip holder is configured to hold the needle tip during the installation of the needle tip on the needle shaft.

9. The medical device of claim 8 wherein: the needle tip receptacle is configured to hold the needle tip during the installation of the needle tip on the needle shaft with a friction fit connection formed with the needle tip.

10. The medical device of claim 9 wherein: the needle tip receptacle includes an elastically deformable member; and the friction fit connection is formed by elastic deformation of the elastically deformable member when the needle tip is in the needle tip receptacle.

11. The medical device of claim 8 wherein:
the needle tip receptacle is configured to hold the needle tip during the installation of the needle tip on the needle shaft with a magnetic force applied to the needle tip.

12. The medical device of claim 11 wherein: the needle tip receptacle includes a magnet; and the needle tip comprises a magnetic material.

13. The medical device of claim 8 wherein: the needle tip receptacle is configured to hold the needle tip during the installation of the needle tip on the needle shaft with a vacuum force applied to the needle tip.

14. The medical device of claim 13 wherein: the needle tip receptacle is in fluid communication with a vacuum passage through which a vacuum is drawn with a vacuum generating device.

15. The medical device of claim 8 wherein: the needle tip receptacle is configured to hold the needle tip during the installation of the needle tip on the needle shaft with a positive mechanical engagement connection formed with the needle tip.

16. The medical device of claim 15 wherein: the at least one needle tip includes needle tip threads; the needle tip receptacle includes needle tip receptacle threads; and the positive mechanical engagement is formed by threaded engagement of the needle tip threads with the needle tip receptacle threads.

17. The medical device of claim 15 wherein: the at least one needle tip includes at least one needle tip ridge and/or at least one needle tip groove; the needle tip receptacle includes at least one needle tip receptacle ridge and/or at least one needle tip receptacle groove; and the positive mechanical engagement is formed by positive mechanical engagement of the at least one needle tip ridge with the at least one needle tip receptacle groove and/or engagement of the at least one needle tip groove with the at least one needle tip receptacle ridge.

18. The medical device of claim 15 wherein: the positive mechanical engagement is formed by a portion of the at least one needle tip which overlaps a portion of the needle tip receptacle in a plane transverse to a longitudinal axis of the tool.

19. The medical device of claim 1 wherein: the needle tip is configured to close the fluid flow passage within the needle shaft when the needle tip is installed on the needle shaft to ingress of fluid into the fluid flow passage.

20. The medical device of claim 1 wherein: the fluid flow passage within the needle shaft is provided by a lumen of the needle shaft.

21. The medical device of claim 20 wherein: the needle tip is configured to close the lumen of the needle shaft when the needle tip is installed on the needle shaft to ingress of fluid into the lumen.

* * * * *